(12) United States Patent
Liu et al.

(10) Patent No.: US 10,046,082 B2
(45) Date of Patent: Aug. 14, 2018

(54) COLLAGEN SPONGE CONTAINING A DRUG FOR PROMOTING FRACTURE HEALING AND METHOD FOR PREPARING THE SAME

(71) Applicant: WUHAN VSD MEDICAL SCIENCE & TECHNOLOGY CO., LTD., Wuhan, Hubei (CN)

(72) Inventors: Yansong Liu, Wuhan (CN); Yingze Zhang, Wuhan (CN); Zhidao Xia, Wuhan (CN); Hongxia Guan, Wuhan (CN)

(73) Assignee: WUHAN VSD MEDICAL SCIENCE & TECHNOLOGY CO., LTD., Wuhan (CN)

( * ) Notice: Subject to any disclaimer, the term of this patent is extended or adjusted under 35 U.S.C. 154(b) by 0 days.

(21) Appl. No.: 15/307,230

(22) PCT Filed: Dec. 17, 2015

(86) PCT No.: PCT/CN2015/097708
§ 371 (c)(1),
(2) Date: Oct. 27, 2016

(87) PCT Pub. No.: WO2016/192377
PCT Pub. Date: Dec. 8, 2016

(65) Prior Publication Data
US 2017/0143869 A1 May 25, 2017

(30) Foreign Application Priority Data
Jun. 4, 2015 (CN) .......................... 2015 1 0304239

(51) Int. Cl.
*A61L 24/10* (2006.01)
*A61L 24/00* (2006.01)

(52) U.S. Cl.
CPC ....... *A61L 24/0036* (2013.01); *A61L 24/0015* (2013.01); *A61L 24/0084* (2013.01); *A61L 24/0089* (2013.01); *A61L 2300/102* (2013.01); *A61L 2300/112* (2013.01); *A61L 2300/412* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 2004/0097469 A1* | 5/2004 | Little | .................. | A61K 31/198 514/89 |
| 2004/0192658 A1* | 9/2004 | Hunter | .................. | A61K 38/39 514/152 |
| 2008/0305517 A1* | 12/2008 | Griffin | .................. | A61L 15/325 435/68.1 |

FOREIGN PATENT DOCUMENTS

| | | |
|---|---|---|
| CN | 1732023 A | 2/2006 |
| CN | 101229177 A | 7/2008 |
| CN | 101631562 A | 1/2010 |
| CN | 105012995 A | 11/2015 |
| WO | 2015009991 A2 | 1/2015 |

OTHER PUBLICATIONS

International Search Report issued in International Application No. PCT/CN2015/097708 dated Mar. 15, 2016.
Written Opinion of the International Search Authority issued in International Application No. PCT/CN2015/097708 dated Mar. 15, 2016 and English translation.

* cited by examiner

*Primary Examiner* — Karlheinz R. Skowronek
*Assistant Examiner* — Ronald T Niebauer
(74) *Attorney, Agent, or Firm* — Meunier Carlin & Curfman LLC

(57) ABSTRACT

Provided are a collagen sponge containing a drug for promoting fracture healing and a method for preparing the same, the method comprises the steps of: 1) adding bisphosphonate containing phosphonate radical in an equivalent dosage of 70 to 140 mg and/or strontium salt in a dosage of 100 to 800 mg into 1 kg of the enzymolysis solution of collagen; 2) adding a crosslinking agent into the solution, the crosslinking agent being added in a proportion where 40 to 60 U of crosslinking agent is added per gram of enzymolysis solution; 3) stirring the mixed solution in step 2) uniformly, then putting it into a stainless steel tray, and placing the tray in a vacuum lyophilizer for lyophilizing for 10 to 16 hours so that it is lyophilized into a sponge-like shape; and 4) allowing the collagen sponge in step 3) to be cut, packaged and sealed, and sterilized by irradiation with cobalt 60.

3 Claims, No Drawings

COLLAGEN SPONGE CONTAINING A DRUG FOR PROMOTING FRACTURE HEALING AND METHOD FOR PREPARING THE SAME

TECHNICAL FIELD

The present invention relates to a collagen sponge containing a drug for promoting fracture healing (a collagen sponge containing a catagmatic drug) and a method for preparing the same, which relate to the technical field of medical equipment.

BACKGROUND ART

Osteoporosis (OP) is a generalized skeletal system disease characterized by reduced bone mass and degenerated microstructure of bone tissue, leading to decreased bone strength, increased bone fragility, and increased risk of fractures. Bone remodeling is a process of self-renewal of bone tissue, where osteoclasts constantly absorb the old bone, and osteoblasts constantly form a new bone to supplement the bone parts which have been absorbed. The osteoclasts play an important role in the bone remodeling process after the body's bones grow to maturity. Enhanced activity or increased amount of osteoclasts can lead to increased bone resorption and bone remodeling imbalance, resulting in the occurrence of many skeletal system diseases, such as osteoporosis. The most common complication of osteoporosis is fracture, which normally occurs at the hip, vertebral body, and distal radius. After women go into menopause, bone mass loss is significant, and if there is no appropriate prevention and treatment, osteoporosis will inevitably lead to fractures at radius, vertebral column and hip, etc. With the population aging and the extension of average human lifespan, the worldwide incidence of osteoporotic fracture increases at an average rate of greater than 1% per year. Therefore, one of the main tasks at present is to study more effective and simple means assisting in treating osteoporotic fracture so as to satisfy the needs of different groups of people.

Bisphosphonate (BP) drugs are a new class of drugs developed over the past 30 years, and mainly used for the treatment and prevention of bone metastases of malignant tumor and bone metabolic diseases, such as osteoporosis and Paget's disease. BPs are divided into three generations according to the strength of the effect of the drug or the time to market of the drug. The first generation is BP free of nitrogen, which is a product available mainly during the 1970s and 1980s. The second generation of BP has a significantly better resistance to bone resorption than the first generation product and is primarily featured by containing amino group in the structure thereof. The third generation of BP is the latest generation of drugs, which is available to the market at the end of the last century and the beginning of the present century, has an even stronger resistance to bone resorption, and is more convenient for clinical application, and ibandronate sodium is a typical product thereof.

Ibandronate sodium, as a potent osteoclast inhibitor, is specifically bindable to hydroxyapatite in bones, which can not only inhibit the activity of osteoclasts but also induce apoptosis of osteoclasts, which are the direct effects of ibandronate sodium. Moreover, ibandronate sodium can also act on osteoblasts, and release one or more osteoclast renewal inhibitors by the latter, thereby shortening the lifespan of osteoclasts and reducing the number of osteoclasts. Therefore, ibandronate sodium can treat and prevent osteoporosis when applied to the whole body, and can assist in promoting fracture healing, particularly fractures caused by osteoporosis, when applied locally to the fracture sites. However, treatment with ibandronate sodium-related drugs has some side effects. A few patients may show an increase in body temperature, and sometimes may also show flu-like symptoms. Gastrointestinal discomfort may also occur in individual cases. But the toxic and side effects can be greatly reduced if the drug is applied locally.

Strontium (Sr) is an important component of bones and has a chemical structure similar to that of calcium. The normal function of bones can be maintained if a certain proportion of strontium ions are kept in the bones. Strontium is one of the essential elements in human bones. β-Catenin is an important factor in wnt pathways. Strontium can promote the growth of osteoblasts and inhibit the activity of osteoclasts by regulating the wnt pathways. In addition, strontium salts can increase the activity of alkaline phosphatase (ALP) and synthesis of bone collagen. It is also recognized in animal experiments that strontium salts in the body can reduce bone resorption while increasing bone formation and promoting the increase of bone mass and bone strength. Moreover, the strontium salts can improve the microstructure of the trabecular bone without affecting the stability of minerals in the internal environment. Therefore, applying strontium salts to a local fracture site can not only increase the concentration of a strontium salt drug to promote the healing of the fracture site, but also reduce the systemic toxic and side effects. Collagen is a protein with the highest content in mammals, has special mechanical properties and biological characteristics, and serves the function of supporting organs and protecting the body. With the improvement of preparation processes and the development of modification technology, collagen has become a widely used biological material with an excellent performance, which can be applied to burn dressing, wound filling, hemostasis in vivo, and tissue engineered repair.

DISCLOSURE OF THE INVENTION

The object of the present invention is to provide a collagen sponge containing a drug for promoting fracture healing (i.e., a catagmatic drug) and a method for preparing the same. Tamponing a fracture site with the collagen sponge serves the tamponade and hemostasis functions on the one hand, and, on the other hand, the collagen sponge serves as a drug carrier due to its special structure, which carries bisphosphonate and/or strontium salt and acts on the fracture site, so as to promote the healing of fractures, particularly fractures caused by osteoporosis.

The present invention provides a method for preparing a collagen sponge containing a drug for promoting fracture healing. The drug-containing collagen sponge product can promote the fracture healing and in particular be applied to a fracture caused by osteoporosis and promote the fracture healing.

The present invention adopts the following technical solution: a collagen sponge containing a drug for promoting fracture healing of the present invention, whose components include an enzymolysis solution of collagen, a bisphosphonate and/or a strontium salt, and a crosslinking agent; the collagen sponge is prepared by adding a bisphosphonate and/or a strontium salt into an enzymolysis solution of collagen in a proportion where every 1 kg of the enzymolysis solution of collagen contains a bisphosphonate containing phosphonate radical in an equivalent dosage of 70 to 140 mg and a strontium salt in a dosage of 100 to 800 mg, and adding the crosslinking agent such as transglutaminase in a proportion where 40 to 60 U of the crosslinking agent is added per gram of the enzymolysis solution of collagen; where the ratio between the enzymatic hydrolysate of collagen and water in the enzymolysis solution of collagen is 1:9 to 1:8; the bisphosphonate is selected from any one or more of the group consisting of sodium etidronate, sodium clodronate, sodium pamidronate, sodium tiludronate, alendronate sodium, neridronate sodium, olpadronate sodium, risedronate sodium, and ibandronate sodium; and the strontium salt is selected from any one or more of the group consisting of strontium chloride and strontium ranelate.

Preferably, the components of the collagen sponge according to the present invention include: 1 kg of the enzymolysis solution of collagen, a bisphosphonate containing phosphonate radical in an equivalent dosage of 70 to 140 mg, and a strontium chloride in a dosage of 100 to 200 mg and/or a strontium ranelate in a dosage of 300 to 600 mg.

A method for preparing a collagen sponge containing a drug for promoting fracture healing of the present invention comprises the steps of:

1) adding a bisphosphonate containing phosphonate radical in an equivalent dosage of 70 to 140 mg and/or a strontium salt in a dosage of 100 to 800 mg into 1 kg of an enzymolysis solution of collagen, where the ratio between enzymatic hydrolysate of collagen and water in the enzymolysis solution of collagen is 1:9 to 1:8; where the bisphosphonate is selected from any one or more of the group consisting of sodium etidronate, sodium clodronate, sodium pamidronate, sodium tiludronate, alendronate sodium, neridronate sodium, olpadronate sodium, risedronate sodium and ibandronate sodium; and the strontium salt is selected from any one or more of the group consisting of strontium chloride and strontium ranelate;

2) adding a crosslinking agent into the enzymolysis solution of collagen containing a bisphosphonate and/or a strontium salt, the crosslinking agent is added in a proportion where 40 to 60 U of the crosslinking agent is added per gram of the enzymolysis solution of collagen, and the crosslinking lasting for 2 to 5 hours; wherein the crosslinking agent is transglutaminase;

3) stirring the mixed solution obtained in step 2) uniformly, then putting it into a stainless steel tray, and placing the stainless steel tray in a vacuum lyophilizer for lyophilizing for 10 to 16 hours so that the mixed solution is lyophilized into a sponge-like shape; and 4) allowing the collagen sponge containing a bisphosphonate or a strontium salt obtained in step 3) to be cut, packaged and sealed, and sterilized by irradiation with cobalt 60.

The bisphosphonate includes first-generation bisphosphonate which is sodium etidronate.

The bisphosphonate includes second-generation bisphosphonates which are sodium clodronate, sodium pamidronate, and sodium tiludronate.

The bisphosphonate includes third-generation bisphosphonates which are alendronate sodium, neridronate sodium, olpadronate sodium, risedronate sodium and ibandronate sodium.

Preferably, the collagen sponge containing a drug for promoting fracture healing according to the present invention comprises a combination of a bisphosphonate and a strontium salt. The collagen sponge comprises the following components in the following ratios: 1 kg of the enzymolysis solution of collagen, a bisphosphonate containing phosphonate radical in an equivalent dosage of 70 to 140 mg, a strontium chloride in a dosage of 100 to 200 mg, and a strontium ranelate in a dosage of 300 to 600 mg.

The present invention adopts the following technical solution: a collagen sponge containing a drug for promoting fracture healing of the present invention, comprising the following components: an enzymolysis solution of collagen, a bisphosphonate and/or a strontium salt, and a crosslinking agent; the collagen sponge is prepared by adding the bisphosphonate and/or the strontium salt into the enzymolysis solution of collagen in a proportion where, for 1 kg of the enzymolysis solution of collagen, the equivalent dosage of phosphonate radical in the bisphosphonate is 70 to 140 mg/kg, and the dosage of the strontium salt is 100 to 800 mg/kg, and adding 40 to 60 U of transglutaminase as the crosslinking agent per gram of the enzymolysis solution of collagen; wherein the ratio of enzymatic hydrolysate of collagen to water is 1:9 to 1:8; the bisphosphonate includes sodium etidronate, sodium clodronate, sodium pamidronate, sodium tiludronate, alendronate sodium, neridronate sodium, olpadronate sodium, risedronate sodium and ibandronate sodium; and the strontium salt includes strontium chloride and strontium ranelate.

Preferably, in the preparation method, for 1 kg of the enzymolysis solution of collagen, the equivalent dosage of the phosphonate radical in the prototype drug is 70 to 140 mg/kg, the dosage of the strontium chloride is 100 to 200 mg/kg, and the dosage of the strontium ranelate is 300 to 600 mg/kg.

A method for preparing a collagen sponge containing a drug for promoting fracture healing of the present invention comprises the steps of:

1) adding a bisphosphonate and/or a strontium salt into 1 kg of the enzymolysis solution of collagen, wherein the ratio of enzymatic hydrolysate of collagen to water is 1:9 to 1:8; the equivalent dosage of phosphonate radical in the prototype drug is 70 to 140 mg/kg; and the dosage of the strontium salt is 100 to 800 mg/kg; where the bisphosphonate includes sodium etidronate, sodium clodronate, sodium pamidronate, sodium tiludronate, alendronate sodium, neridronate sodium, olpadronate sodium, risedronate sodium and ibandronate sodium; and the strontium salt includes strontium chloride and strontium ranelate;

2) adding a crosslinking agent into the enzymolysis solution of collagen containing the bisphosphonate and/or the strontium salt, a transglutaminase as the crosslinking agent being added in a proportion of 40 to 60 U per gram of the enzymolysis solution of collagen, and the crosslinking lasting for 2 to 5 hours; wherein the crosslinking agent is a transglutaminase;

3) stirring the mixed solution in step 2) uniformly, putting it into a stainless steel tray, and placing the stainless steel tray in a vacuum lyophilizer for lyophilizing for 10 to 16 hours so that the mixed solution is lyophilized into a sponge-like shape; and 4) allowing the collagen sponge containing the bisphosphonate or strontium salt to be cut, packaged and sealed, and sterilized by irradiation with cobalt 60.

The bisphosphonate includes first-generation bisphosphonate which is sodium etidronate.

The bisphosphonate includes second-generation bisphosphonates which are sodium clodronate, sodium pamidronate and sodium tiludronate.

The bisphosphonate includes third-generation bisphosphonates which are alendronate sodium, neridronate sodium, olpadronate sodium, risedronate sodium and ibandronate sodium.

Preferably, the drug for promoting fracture healing is a combination of the bisphosphonate and the strontium salt in a proportion where, for 1 kg of the enzymolysis solution of collagen, the equivalent dosage of phosphonate radical in the prototype drug is 70 to 140 mg/kg, the dosage of the strontium chloride is 100 to 200 mg/kg, and the dosage of the strontium ranelate is 300 to 600 mg/kg.

The present invention has the following beneficial effects.

The present invention provides a collagen sponge containing a drug for promoting fracture healing, which is a novel combined material and prepared by a novel and inventive preparation method of the present invention on the basis of pure collagen sponge using the collagen sponge as a drug carrier.

The following experiments indicate that, thanks to the action of the drug in the combined material, the drug-containing collagen sponge according to the present invention can not only efficiently stop bleeding but also greatly promote the fracture healing when acting on the fracture site, which cannot be achieved by pure collagen sponge dressing. Moreover, the clinical application cases sufficiently show that the collagen sponge of the present invention has exact therapeutic effects.

DETAILED DESCRIPTION OF EMBODIMENTS

In specific embodiments/examples, except for those processes in which the temperature and pressure are specified, all the other treatment processes are carried out at room temperature and under the same atmosphere pressure.

The enzymolysis solution of collagen is prepared by:

placing a cleaned fresh skin or connective tissue from a pig or cow, from which fat has been removed, into a stainless steel bucket; adding 0.01 to 0.03 mol/L of aqueous solution of sodium hydroxide thereto in a solid/liquid ratio of 1:30 to 1:40; soaking it at 6 to 8° C. for 1 to 2 hours; then filtering it with a stainless steel filter such as a coarse filter screen; and keeping the filtrate for further use; adding anhydrous ethyl ether or acetone in an amount equivalent to 6 to 8 times the mass of the above pretreated material (i.e., pigskin/cowskin/connective tissue) into the material; refluxing at 35 to 40° C. for 5 to 8 hours; then washing the pigskin/cowskin/connective tissue with distilled water until it is odor-free; and keeping it for further use; immersing the above treated material (i.e., the pigskin/cowskin/connective tissue) into a mixed solution containing 0.6 to 0.7 mol/L of glacial acetic acid and 600 to 700 mg/L of pepsin; continuously stirring for 25 to 30 hours; treating the above mixture with progressive ultrasonic waves; first treating it with 100 to 200 W ultrasonic wave for 30 minutes; then treating it with 200 to 300 W ultrasonic wave for 30 minutes; at last, treating it with 300 to 400 W ultrasonic wave for 1 hour; immersing the mixture subjected to ultrasonic treatment into 2% to 3% $H_2O_2$ solution; allowing the result to stand for 2 to 4 hours after being sufficiently mixed; adjusting the pH to 5.0 with 5 to 12 mol/L of NaOH; centrifuging it; removing the supernatant; immersing the precipitate into NaCl solution (at a concentration of 2 to 3 mol/L); stirring it for 20 to 30 hours; centrifuging it; immersing the precipitate into 0.6 to 0.7 mol/L of glacial acetic acid and allowing it to dissolve; centrifuging it; taking the supernatant; adjusting the pH to 7.5 with 1% acetic acid solution; immersing the supernatant into NaCl solution (at a concentration of 2 to 3 mol/L); stirring it for 20 to 30 hours; centrifuging it; immersing the precipitate into 0.6 to 0.7 mol/L of glacial acetic acid for dissolution; thereafter, first dialyzing it twice using 0.6 to 0.7 mol/L of glacial acetic acid as an external dialysate, each time for 4 hours; and then dialyzing it for 5 to 7 times using distilled water as an external dialysate, each time for 4 hours, until no chloride ion is detected in the external dialysate; and the enzymolysis solution of collagen is obtained, wherein the ratio between enzymatic hydrolysate of collagen and water in the obtained enzymolysis solution of collagen is 1:9 to 1:8.

EXAMPLE 1

Preparation of a Collagen Sponge Containing First-generation Bisphosphonate:

First-generation bisphosphonate (e.g., sodium etidronate) containing phosphonate radical in an equivalent dosage of 70 mg was added into 1 kg of the prepared enzymolysis solution of collagen, and a crosslinking agent such as transglutaminase was added in a proportion where 40 U of the crosslinking agent was added per gram of the enzymolysis solution of collagen, and the cross-linking lasting for two hours. The obtained product was put into a stainless steel tray after being well stirred.

The stainless steel tray was placed in a vacuum lyophilizer, and lyophilized for 10 hours to obtain a lyophilized collagen sponge. The lyophilized collagen sponge was taken out and cut into products of different specifications according to clinical requirements. The collagen sponge was placed in a package and sealed. The packaged and sealed collagen sponge containing first-generation bisphosphonate was sterilized by irradiation with cobalt 60 for 4 h. The sterilized product can be suitable for clinical and experimental use. It is characterized in that, when the collagen sponge is applied to clinical use, it is ensured that the phosphonate radical in the prototype drug has an optimal dosage, i.e., a bisphosphonate containing phosphonate radical having an equivalent dosage of 70 to 140 mg is added per kg of the enzymolysis solution of collagen. When the administered dosage of the phosphonate radical is less than the optimal dosage, its local drug release concentration cannot reach the required therapeutic concentration; and when the administered dosage of the phosphonate radical is more than the optimal dosage, its local drug release concentration is too high, which may cause a toxic effect.

EXAMPLE 2

Preparation of a Collagen Sponge Containing Second-generation Bisphosphonate:

Second-generation bisphosphonate (e.g., any one or more selected from sodium clodronate, sodium pamidronate and sodium tiludronate) containing phosphonate radical in an equivalent dosage of 140 mg was added into 1 kg of the prepared enzymolysis solution of collagen, and a crosslinking agent such as transglutaminase was added in a proportion where 50 U of the crosslinking agent was added per gram of the enzymolysis solution of collagen, and the cross-linking lasting for 5 hours. The obtained product was put into a stainless steel tray after being well stirred.

The stainless steel tray was placed in a vacuum lyophilizer, and lyophilized for 16 hours to obtain a lyophilized collagen sponge. The lyophilized collagen sponge was taken out and cut into products of different specifications according to clinical needs. The collagen sponge was placed in a package and sealed. The packaged and sealed collagen sponge containing second-generation bisphosphonate was sterilized by irradiation with cobalt 60 for 5 h. The sterilized product can be suitable for clinical and experimental use. It is characterized in that, when the collagen sponge is applied to clinical use, it is ensured that the phosphonate radical in the prototype drug has an optimal dosage, i.e., bisphosphonate containing phosphonate radical in an equivalent dosage of 70 to 140 mg is added per kg of the enzymolysis solution of collagen. When the administered dosage of the phosphonate radical is less than the optimal dosage, its local drug release concentration cannot reach the required therapeutic concentration; and when the administered dosage of the phosphonate radical is more than the optimal dosage, its local drug release concentration is too high, which may cause a toxic effect.

EXAMPLE 3

Preparation of a Collagen Sponge Containing Third-generation Bisphosphonate:

Third-generation bisphosphonate (e.g., any one or more selected from alendronate sodium, neridronate sodium, olpadronate sodium, risedronate sodium, and ibandronate sodium) containing phosphonate radical in an equivalent dosage of 100 mg was added into 1 kg of the prepared enzymolysis solution of collagen, and a crosslinking agent such as transglutaminase was added in a proportion where 60 U of crosslinking agent was added per gram of the enzymolysis solution of collagen, the cross-linking lasting for 4 hours. The obtained product was put into a stainless steel tray after being well stirred.

The stainless steel tray was placed in a vacuum lyophilizer, and lyophilized for 14 hours to obtain a lyophilized collagen sponge. The lyophilized collagen sponge was taken out and cut into products of different specifications according to clinical needs. The collagen sponge was placed in a package and sealed. The packaged and sealed collagen sponge containing third-generation bisphosphonate was sterilized by irradiation with cobalt 60 for 6 h. The sterilized product can be suitable for clinical and experimental use. It is characterized in that, when the collagen sponge is applied to clinical use, it is ensured that the phosphonate radical in the prototype drug has an optimal dosage, i.e., bisphosphonate containing phosphonate radical in an equivalent dosage of 70 to 140 mg is added per kg of the enzymolysis solution of collagen. When the administered dosage of the phosphonate radical is less than the optimal dosage, its local drug release concentration cannot reach the required therapeutic concentration; and when the administered dosage of the phosphonate radical is more than the optimal dosage, its local drug release concentration is too high, which may cause a toxic effect.

EXAMPLE 4

Preparation of a Collagen Sponge Containing Strontium Chloride:

100 mg of strontium chloride was added into 1 kg of the prepared enzymolysis solution of collagen, and a crosslinking agent such as transglutaminase was added in a proportion where 45 U of crosslinking agent was added per gram of the enzymolysis solution of collagen, the cross-linking lasting for 3 hours. The obtained product was put into a stainless steel tray after being well stirred.

The stainless steel tray was placed in a vacuum lyophilizer, and lyophilized for 12 hours to obtain a lyophilized collagen sponge. The lyophilized collagen sponge was taken out and cut into products of different specifications according to clinical needs. The collagen sponge was placed in a package and sealed. The packaged and sealed collagen sponge containing strontium chloride was sterilized by irradiation with cobalt 60 for 4.5 h. The sterilized product can be suitable for clinical and experimental use. It is characterized in that, when the collagen sponge is applied to clinical use, it is ensured that the strontium chloride has an optimal dosage, i.e., 100 to 200 mg of strontium chloride is contained per kg of the enzymolysis solution of collagen. When the administered dosage of strontium chloride is less than the optimal dosage, its local drug release concentration cannot reach the required therapeutic concentration; and when the administered dosage of strontium chloride is more than the optimal dosage, its local drug release concentration is too high, which may cause a toxic effect.

In another two examples, strontium chloride was added in amounts of 200 mg and 800 mg, respectively, and other raw materials used, experimental conditions and processes were all the same.

EXAMPLE 5

Preparation of a Collagen Sponge Containing Strontium Ranelate:

600 mg of strontium ranelate was added into 1 kg of the prepared enzymolysis solution of collagen, and a crosslinking agent such as transglutaminase was added in a proportion where 55 U of crosslinking agent was added per gram of the enzymolysis solution of collagen, and the crosslinking lasting for 5 hours. The obtained product was put into a stainless steel tray after being well stirred.

The stainless steel tray was placed in a vacuum lyophilizer, and lyophilized for 15 hours to obtain a lyophilized collagen sponge. The lyophilized collagen sponge was taken out and cut into products of different specifications according to clinical needs. The collagen sponge was placed in a package and sealed. The packaged and sealed collagen sponge containing strontium ranelate was sterilized by irradiation with cobalt 60 for 5.5 h. The sterilized product can be suitable for clinical and experimental use. It is characterized in that, when the collagen sponge is applied to clinic use, it is ensured that the strontium ranelate has an optimal dosage, i.e., 300 to 600 mg of strontium ranelate is contained per kg of the enzymolysis solution of collagen. When the administered dosage of strontium ranelate is less than the optimal dosage, its local drug release concentration cannot reach the required therapeutic concentration; and when the administered dosage of strontium ranelate is more than the optimal dosage, its local drug release concentration is too high, which may cause a toxic effect.

In another three examples, the strontium ranelate was added in amounts of 100 mg, 300 mg, and 800 mg, respectively, and other raw materials used, experimental conditions and processes were all the same.

EXAMPLE 6

Preparation of a Collagen Sponge Containing Bisphosphonate(s) and Strontium Salt(s):

Bisphosphonate(s) (including any one or more of sodium etidronate, sodium clodronate, sodium pamidronate, sodium tiludronate, alendronate sodium, neridronate sodium, olpadronate sodium, risedronate sodium, ibandronate sodium, etc.) containing phosphonate radical in an equivalent dosage of 70 mg and 100 mg of strontium salt(s) (including any one or more of strontium chloride, and strontium ranelate, etc.) were added into 1 kg of the prepared enzymolysis solution of collagen, and crosslinking agent such as transglutaminase was added in a proportion where 60 U of crosslinking agent was added per gram of the enzymolysis solution of collagen, and the cross-linking lasting for 5 hours. The obtained product was put into a stainless steel tray after being well stirred.

The stainless steel tray was placed in a vacuum lyophilizer, and lyophilized for 16 hours to obtain a lyophilized collagen sponge. The lyophilized collagen sponge was taken out and cut into products of different specifications according to clinical needs. The collagen sponge was placed in a package and sealed. The packaged and sealed collagen sponge containing bisphosphonate(s) and strontium salt(s) was sterilized by irradiation with cobalt 60 for 6 h. The sterilized product can be suitable for clinical and experimental use. It is characterized in that, when the collagen sponge is applied to clinical use, it is ensured that the phosphonate radical in the prototype drug has an optimal dosage, i.e., every kg of the enzymolysis solution of collagen contains: bisphosphonate containing phosphonate radical with an equivalent dosage of 70 to 140 mg, 100 to 200 mg/kg of strontium chloride, and 300 to 600 mg of strontium ranelate. When the administered dosage of the bisphosphonate and the strontium salt is less than the optimal dosage, its local drug release concentration cannot reach the required therapeutic concentration; and when the administered dosage of the bisphosphonate and the strontium salt is more than the optimal dosage, its local drug release concentration is too high, which may cause a toxic effect.

Animal Experiments on the Drug-Containing Collagen Sponge in Promoting the Healing of Fracture 1. Materials and Method 1.1. Experimental Animal: New Zealand rabbits, each being male and having a weight of about 2 to 3 kg (12 to 16 weeks old) were used 1.2. Experimental Grouping and Materials: experiments were divided into a control group (Control), a collagen sponge (CS) group, an ibandronate sodium (0.1 mg/kg IB) group, a group with a small dosage of ibandronate sodium+collagen sponge (SIB+CS, 0.125 mg IB), a group with a median dosage of ibandronte sodium+collagen sponge (MIB+CS, 0.25 mg IB), and a group with a large dosage of ibandronate sodium+collagen sponge (LIB+CS, 0.5 mg IB), in total 6 groups. 10 experimental animals are used for each group, 70 in total.

1.3. Preparation of Materials:

Preparation of materials for the SIB+CS group: 125 μl of 1 mg/ml IB was added into 600 ml of the enzymolysis solution of collagen to prepare a 50*25*5 mm collagen sponge;

Preparation of materials for the MIB+CS group: 250 μl of 1 mg/ml IB was added into 600 ml of the enzymolysis solution of collagen to prepare a 50*25*5 mm collagen sponge;

Preparation of materials for the LIB+CS group: 500 μl of 1 mg/ml IB was added into 600 ml of the enzymolysis solution of collagen to prepare a 50*25*5 mm collagen sponge.

2. Experimental Method:

Male New Zealand rabbits were anesthetized by marginal ear vein injection with sodium pentobarbital (3%, 1 mg/kg). After the anesthesia, the skin in the surgical area was depilated with 8% sodium sulfide and disinfected. The animals were fixed on their backs, and disinfected and covered with a sterile towel or sheet. A longitudinal incision was cut at the distal femur of the right leg near the patella. The patella was retracted to expose the inner and outer condyles of the distal femur. A 2 mm Kirschner wire was inserted retrogradely between the inner and outer condyles through an electric drill. The Kirschner wire went through the medullary cavity and came out of the skin from the proximal femur. The distal end of the Kirschner wire was cut off and ensured to be embedded under the surface of the knee joint. The knee was reset. An incision was made on the outer side of the distal femur, and the femur was exposed along the intermuscular space. Sufficient protection was provided for the surrounding soft tissues such as muscles and blood vessels. The femur was cut by a dental drill. The Control group and the IB group were not subjected to any treatment. The prepared materials for the CS group, the SIB+CS group, the MIB+CS group and the LIB+CS group were placed at the fracture sites of the animals, respectively. The incisions and the skin were washed with sterile normal saline and sutured with 5-0 nylon thread. Normal saline (0.1 ml/kg) and ibandronate sodium (0.1 ml/kg) were administered to the Control group and the IB group after surgery, respectively. All the animals were injected intramuscularly with buprenorphine (0.05 mg/kg) twice and with ciprofloxacin (10 mg/kg) once a day for 3 days after the surgery. All the animals were fed normally (lightless, quiet, at a temperature from 20 to 26° C., and at a humidity below 80%). X-ray photographs were taken on the day of surgery to check the condition of fracture apposition and alignment after the surgery. Further, half of the New Zealand rabbits were sacrificed at the 2nd week and the 4th week for detection, respectively.

3. Experimental Results:

3.1. Changes in callus cross-sectional area at the 2nd week and the 4th week in respective groups were shown in the following table. At the 2nd week and the 4th week, the callus cross-sectional area in each of the collagen sponge groups containing different dosages of IB increased significantly compared to the Control, GS, and IB groups. Among them, the MIB group showed the most significant change.

TABLE 1

Changes in callus cross-sectional area at the 2nd week and the 4th week in respective groups (CSA, mm$^2$)

| Group | 2nd week | | 4th week | |
| --- | --- | --- | --- | --- |
| | n | CSA | n | CSA |
| CONTROL | 5 | 66.8 ± 3.6$^{a,b,c,d}$ | 5 | 76.6 ± 2.9$^{a,b,c,d}$ |
| GS | 5 | 66.2 ± 3.5$^{e,f,g,h}$ | 5 | 80.2 ± 4.9$^{e,f,g,h}$ |
| SIB + GS | 5 | 103 ± 3.4$^{b,e,i}$ | 5 | 143 ± 4.2$^{b,e,i}$ |
| MIB + GS | 5 | 113.1 ± 3.8$^{c,f,j}$ | 5 | 208.2 ± 6.0$^{c,f,j}$ |
| LIB + GS | 5 | 110 ± 3.7$^{d,g,k}$ | 5 | 195 ± 5.8$^{d,g,k}$ |
| IB | 5 | 89.9 ± 3.6$^{a,h,i,j,k}$ | 5 | 120.5 ± 7.8$^{a,h,i,j,k}$ |
| p | — | <0.001 | — | <0.001 |

$^a$comparing the control group with the IB group, p < 0.001
$^b$comparing the control group with the SIB + GS group, p < 0.001
$^c$comparing the control group with the MIB + GS group, p < 0.001
$^d$comparing the control group with the LIB + GS group, p < 0.001
$^e$comparing the GS group with the SIB + GS group, p < 0.001
$^f$comparing the GS group with the MIB + GS group, p < 0.001
$^g$comparing the GS group with the LIB + GS group, p < 0.001
$^h$comparing the GS group with the IB group, p < 0.001
$^i$comparing the SIB + GS group with the IB group, p < 0.001
$^j$comparing the MIB + GS group with the IB group, p < 0.001
$^k$comparing the LIB + GS group with the IB group, p < 0.001

3.2. Three-point bending force test at tibia fracture sites of the rabbits at the second week and the fourth week As shown in Table 2 and Table 3, at the second week and the fourth week, a three-point bending force test at tibia fracture sites of the rabbits was performed, and it was found that the MIB group showed the best result.

TABLE 2

Three-point bending force test at tibia fracture sites of the rabbits at the 2nd week

| Group | n | Limit Load (N) | Compressive Strength (Nmm) | Elastic Modulus (MPa) |
| --- | --- | --- | --- | --- |
| CONTROL | 5 | 5.2 ± 1.1 | 4.2 ± 1.4 | 4.0 ± 1.5 |
| GS | 5 | 6.1 ± 1.0 | 5.9 ± 1.5 | 6.7 ± 1.9 |
| SIB + GS | 5 | 7.2 ± 1.7 | 6.1 ± 1.4 | 7.2 ± 1.1 |
| MIB + GS | 5 | 9.0 ± 2.0 | 7.8 ± 2.0 | 8.6 ± 2.6 |
| LIB + GS | 5 | 8.6 ± 1.2 | 7.4 ± 1.6 | 8.0 ± 2.4 |
| IB | 5 | 6.8 ± 1.7 | 4.7 ± 1.8 | 7.3 ± 2.2 |

TABLE 3

Three-point bending force test at tibia fracture sites of the rabbits at the 4th week

| Group | n | Limit Load (N) | Compressive Strength (Nmm) | Elastic Modulus (MPa) |
| --- | --- | --- | --- | --- |
| CONTROL | 5 | 45.5 ± 5.13$^{a,b,c,d}$ | 24.5 ± 4.8$^{a,b,c,d}$ | 48.2 ± 9.2 |
| GS | 5 | 49.9 ± 6.7$^{e,f,g,h}$ | 33.6 ± 7.1$^{e,f,g,h}$ | 54.8 ± 9.9 |
| SIB + GS | 5 | 62.3 ± 8.0$^{b,e,i}$ | 60.2 ± 5.2$^{b,e}$ | 75.3 ± 9.6 |
| MIB + GS | 5 | 129.8 ± 9.6$^{c,f,j}$ | 88.4 ± 9.2$^{c,f,j}$ | 103.0 ± 30.1 |
| LIB + GS | 5 | 100.2 ± 6.7$^{d,g}$ | 78.3 ± 6.3$^{d,g}$ | 85.3 ± 20.3 |
| IB | 5 | 95.9 ± 7.04$^{i,j}$ | 64.6 ± 7.3$^{j}$ | 88.2 ± 19.5 |

$^a$comparing the control group with the IB group, p < 0.05
$^b$comparing the control group with the SIB + GS group, p < 0.05
$^c$comparing the control group with the MIB + GS group, p < 0.05
$^d$comparing the control group with the LIB + GS group, p < 0.05
$^e$comparing the GS group with the SIB + GS group, p < 0.05
$^f$comparing the GS group with the MIB + GS group, p < 0.05
$^g$comparing the GS group with the LIB + GS group, p < 0.05
$^h$comparing the GS group with the IB group, p < 0.05
$^i$comparing the SIB + GS group with the IB group, p < 0.05
$^j$comparing the MIB + GS group with the IB group, p < 0.05
$^k$comparing the LIB + GS group with the IB group, p < 0.05

4. Conclusion

It was found by the above animal experiments that the collagen sponge, into which a median dosage of ibandronate sodium was added, had the best effect of promoting the fracture healing.

Clinical Test on the Drug-containing Collagen Sponge in Promoting the Fracture Healing 1. Materials and Method 1.1. Clinical data: 60 patients suffered from osteoporotic fractures were divided randomly into two groups, i.e., an experimental group and a control group, each having 30 patients. A collagen sponge prepared from a the enzymolysis solution of collagen containing a bisphosphonate (ibandronate sodium 300 mg/kg) and a strontium salt (strontium chloride 200 mg/kg) and a collagen sponge containing normal saline were administered to fracture sites by double blind method. The genders and ages of the two groups were compared and the differences had no statistical significance (p>0.05). (Table 1)

TABLE 1

Distributions of gender and age of the two groups of patients (n = 30)

| Group | Number of Patients | Gender (male:female) | Age (years old) | Average Age |
| --- | --- | --- | --- | --- |
| Experimental Group | 30 | 7:8 | 53-77 | 67.48 ± 6.275 |
| Control Group | 30 | 6:9 | 55-75 | 67.16 ± 5.109 |

1.2. Source of Material

The drug-containing collagen sponge from Example 6 was used.

1.3. Research Method

The fracture sites were exposed surgically and reset at the broken ends of the fractures. A collagen sponge containing a bisphosphonate or a strontium salt was attached to the broken ends in the experimental group, whereas a collagen sponge containing normal saline was attached in the control group. The fracture sites were externally fixed with plaster and were detected with X-ray at the 2nd week and the 4th week respectively to observe the growth of callus.

1.4. Statistical Analysis

The statistical analysis was performed using SPSS19.0 software. The data were expressed by (x±s) and analyzed with t test. The difference has statistical significance (p<0.05).

2. Results

Comparison of imaging scores: at the 2nd week, in the experimental group, the bony callus was cloud-like, the cartilage callus substantially disappeared, and the fracture line was blurred. In the control group, the patients showed obvious symptoms of local pain and pain on vertical percussion, which suggested that clinical healing was not achieved. The difference between Lane-Sandhu X-ray scoring results of the patients in the experimental group and the control group at the 2nd week after fracture reset and plaster external fixation has statistical significance (p<0.05). And, the scoring result of callus growth in the experimental group at the 4 week has a remarkable statistical significance compared with the control group (p<0.05) (Table 2).

TABLE 2

Scoring results of the degree of callus growth of the patients suffered from osteoporotic fractures in the experimental and control groups (n = 30, x ± s)

| Group | n | 2nd week | 4th week |
| --- | --- | --- | --- |
| Experimental Group | 30 | 2.07 ± 0.521 * | 3.67 ± 0.479$^\#$ |
| Control Group | 30 | 1.80 ± 0.484 | 3.23 ± 0.430 |

The results show that the speed of callus growth at the fracture ends, the number of cells, and the bone quality of the patients are better in the experimental group than in the control group, and that the collagen sponge containing a bisphosphonate and a strontium salt can promote the healing of osteoporotic fractures and accelerate the healing process.

The invention claimed is:

1. A method for preparing a collagen sponge containing a drug for promoting fracture healing, comprising the steps of:
   1) adding a bisphosphonate and/or a strontium salt into 1 kg of an enzymolysis solution of collagen, wherein the ratio of an enzymatic hydrolysate of collagen to water is 1:9 to 1:8; and the equivalent dosage of the phosphonate radical in the bisphosphonate is 70 to 140mg/ kg; and the dosage of the strontium salt is 100 to 800 mg/kg; wherein the bisphosphonate is selected from anyone or more of the group consisting of sodium etidronate, sodium clodronate, sodium pamidronate, sodium tiludronate, alendronate sodium, neridronate sodium, olpadronate sodium, risedronate sodium and ibandronate sodium; and the strontium salt is selected from any one or more of the group consisting of strontium chloride and strontium ranelate;

2) adding a crosslinking agent into the enzymolysis solution of collagen containing a bisphosphonate and/or a strontium salt, transglutaminase as the crosslinking agent being added in a proportion of 40 to 60 U per gram of the enzymolysis solution of collagen, and the crosslinking lasting for 2 to 5 hours; wherein the crosslinking agent is transglutaminase;

3) stirring the mixed solution in step 2) uniformly, putting it into a stainless steel tray, and placing the stainless steel tray in a vacuum lyophilizer for lyophilizing for 10 to 16hours so that the mixed solution is lyophilized into a sponge shape; and 4) allowing the collagen sponge containing the bisphosphonate or strontium salt to be cut, packaged and sealed, and sterilized by irradiation with cobalt 60.

2. The method for preparing a collagen sponge containing a drug for promoting fracture healing according to claim 1, wherein the bisphosphonate is selected from the group consisting of sodium etidronate, sodium clodronate, sodium pamidronate, sodium tiludronate, alendronate sodium, neridronate sodium, olpadronate sodium, risedronate sodium and ibandronate sodium.

3. The method for preparing a collagen sponge containing a drug for promoting fracture healing according to claim 1, wherein the drug for promoting fracture healing is a combination of the bisphosphonate and the strontium salt combined in a proportion where, for 1 kg of the enzymolysis solution of collagen, the equivalent dosage of the phosphonate radical in the bisphosphonate is 70 to 140 mg/kg, the dosage of the strontium chloride is 100 to 200 mg/kg, and the dosage of the strontium ranelate is 300 to 600 mg/kg.

* * * * *